US011275068B2

(12) United States Patent
Willett (10) Patent No.: US 11,275,068 B2
(45) Date of Patent: Mar. 15, 2022

(54) REMOTE GAS SENSING USING UAVS

(71) Applicant: Honeywell International Inc., Morris Plains, NJ (US)

(72) Inventor: Martin Willett, Waterlooville (GB)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 221 days.

(21) Appl. No.: 16/175,619

(22) Filed: Oct. 30, 2018

(65) Prior Publication Data

US 2019/0128862 A1 May 2, 2019

Related U.S. Application Data

(60) Provisional application No. 62/579,257, filed on Oct. 31, 2017.

(51) Int. Cl.
*G01N 33/00* (2006.01)
*B64C 39/02* (2006.01)

(52) U.S. Cl.
CPC ....... *G01N 33/0032* (2013.01); *B64C 39/024* (2013.01); *G01N 33/0009* (2013.01); *B64C 2201/027* (2013.01); *B64C 2201/12* (2013.01)

(58) Field of Classification Search
CPC ............ G01N 33/0032; G01N 33/0009; B64C 39/024; B64C 2201/027; B64C 2201/12
See application file for complete search history.

(56) References Cited

U.S. PATENT DOCUMENTS 9,676,481 B1 * 6/2017 Buchmueller ........... B64D 1/02
9,688,404 B1 * 6/2017 Buchmueller ....... G06Q 10/083
2007/0221863 A1   9/2007 Zipf
(Continued)

FOREIGN PATENT DOCUMENTS

CN      205749269 U  * 11/2016
CN      106527486 A  *  3/2017
WO      2016029305 A1    3/2016

OTHER PUBLICATIONS

An Overview of Small Unmanned Aerial Vehicles for Air Quality Measurements: Present Applications and Future Prospectives, Villa et al., Jul. 12, 2016. (Year: 2016).*
(Continued)

*Primary Examiner* — Ryan D Walsh
(74) *Attorney, Agent, or Firm* — Alston & Bird LLP (57) ABSTRACT

Apparatus and associated methods relate to height-differentiated gas detection sensors attached to one or more tethers suspended from an unmanned air vehicle (UAV) platform. In an illustrative example, each of the gas sensors, for example, may communicate gas detection signal information to a signal processing module onboard the UAV platform. Each of the tethers, for example, may provide a data channel from the sensor to the signal processing module. Some tethers, for example, may supply operating power to one or more of the gas detection sensors. The UAV platform may advantageously deploy one or more low-cost, disposable, tethered gas detection sensors into vertically confined spaces (e.g., chimneys, vents), or along a length of pipeline, for example. The sensors may be deployed at a minimum predetermined height providing separation from the UAV to attenuate prop-wash with respect to the sensors.

20 Claims, 8 Drawing Sheets

(56) References Cited

U.S. PATENT DOCUMENTS

| | | | |
|---|---|---|---|
| 2016/0368604 A1 | 12/2016 | Duesterhoft et al. | |
| 2017/0032258 A1* | 2/2017 | Miresmailli | A01G 13/06 |
| 2017/0191829 A1* | 7/2017 | Van Schoyck | G01C 5/005 |
| 2017/0261629 A1* | 9/2017 | Gunnarsson | G01V 1/3817 |
| 2017/0339487 A1* | 11/2017 | Alvord | B64C 39/024 |
| 2018/0156770 A1* | 6/2018 | Saez | G01N 33/24 |
| 2018/0204585 A1* | 7/2018 | Whittaker | B64C 39/024 |

OTHER PUBLICATIONS

Pergam Technical Services, Laser Methane mini (LMm), 2017 [online], [retrieved on Oct. 25, 2017]. Retrieved from the Internet <http://pergamusa.com/lmm/>.

Pergam Technical Services, LMC Laser Methane Copter, 2017 [online], [retrieved on Oct. 25, 2017]. Retrieved from the Internet <http://pergamusa.com/gascopter/>.

Lillian, Betsy, Pergam Rolls out Methane Sensor for UAVs, Unmanned Aerial Online, Jul. 17, 2015 [online], [retrieved on Oct. 25, 2017], Retrieved from the Internet <https://unmanned-aerial.com/pergam-rolls-out-methane-sensor-for-uavs>.

Lillian, Betsy, Microdrones Rolls out Integrated Solution for Drone-Based Methane Detection, Unmanned Aerial Online, Oct. 24, 2017 [online], [retrieved on Oct. 25, 2017]. Retrieved from the Internet <https://unmanned-aerial.com/microdrones-rolls-integrated-solution-drone-based-methane-detection>.

Aeromon, RPAS-assisted detecting and monitoring of gaseous compounds, Jan. 11, 2016 [online], [retrieved on Aug. 8, 2017]. Retrieved from the Internet <https://www.google.com/url?sa=t&rct=j&q=&esrc=s&source=web&cd=4&cad=rja&uact=8&ved=0ahUKEwihz-PB7JHXAhWE1IMKHZL3AGQQFgg6MAM&url=http%3A%2F%2Fwww.syke.fi%2Fdownload%2Fnoname%2F%257B028AF3DA-8816-4A78-9627-71F7C520F42B%257D%2F123065&usg=AOvVaw1NtSnH3kcOI8vJ5J2TbrD6>.

Villa, T., Gonzalez, F., Miljievic, B., Ristovski, Z., and Morawska, L., An Overview of Small Unmanned Aerial Vehicles for Air Quality Measurements: Present Applications and Future Perspectives, US National Library of Medicine National Institutes of Health, Jul. 2016 [online], [retrieved on Aug. 8, 2017]. Retrieved from the Internet <https://www.ncbi.nlm.nih.gov/pmc/articles/PMC4969839/>.

Houston, A., Argrow, B., Elston, J., Lahowetz, J., Frew, E., and Kennedy, P., The Collaborative Colorado-Nebraska Unmanned Aircraft System Experiment, American Meteorological Society Journals Online, Jan. 2012 [online], [retrieved on Sep. 14, 2017]. Retrieved from the Internet <http://journals.ametsoc.org/doi/abs/10.1175/2011BAMS3073.1>.

Rossi, M., Brunelli, D., Adami, A., Lorenzelli, L., Menna, F., and Remondino, F., Gas-Drone: Portable gas sensing system on UAVs for gas leakage localization, Nov. 2014 [online], [retrieved on Sep. 14, 2017] Retrieved from the Internet <https://www.researchgate.net/publication/269832212_Gas-Drone_Portable_gas_sensing_system_on_UAVs_for_gas_leakage_localization>.

Sankaran, S., Mishra, A., Ehsani, R., and Davis, C., A review of advanced techniques for detecting plant diseases, Computers and Electronics in Agriculture Journal, Feb. 22, 2010 [online], [retrieved on Sep. 14, 2017]. Retrieved from the Internet <http://www.sciencedirect.com/science/article/pii/S0168169910000438>.

Segor, F., Burkle, A., Kollman, M., Shonbein, R., Instantaneous Autonomous Aerial Reconnaissance for Civil Applications: A UAV based approach to support security and rescue forces, Jan. 2011 [online], [retrieved on Sep. 14, 2017]. Retrieved from the Internet <http://akme-a2.iosb.fraunhofer.de/EatThisGoogleScholar/d/2011_Instantaneous%20autonomous%20aerial%20reconnaissance%20for%20civil%20applications-%20A%20UAV%20based%20approach%20to%20support%20security%20and%20rescue%20forces.pdf>.

* cited by examiner

REMOTE GAS SENSING USING UAVS

CROSS-REFERENCE TO RELATED APPLICATIONS

This application claims the benefit of U.S. Provisional Application Ser. No. 62/579,257, titled "REMOTE GAS SENINGS USING UAVS," filed by Martin Willett, on Oct. 31, 2017.

This application incorporates the entire contents of the foregoing application(s) herein by reference.

TECHNICAL FIELD

Various embodiments relate generally to applications using unmanned air vehicles (UAVs).

BACKGROUND

A sector of unmanned air vehicles (UAVs) includes drones which typically operate on four propellers. Some drones may include a flight controller which may continuously monitor the attitude of the aircraft and may individually adjust the propeller speeds to remain in a stabilized state. Drones may maneuver in 3-D space moving vertically or horizontally, and may hover over a specified area to perform various tasks.

Drones may be controlled remotely by way of a wireless controller. In some examples, the wireless controller may be a radio-frequency (RF) controller. In various examples, the wireless controller may be an optical controller. Drones may also be remotely controlled via a wired tether.

Drones may support various onboard instrumentation. For example, some drones may carry cameras. Cameras on board drones may provide photographs or videos from a vantage point not easily achieved with other vehicles. Some drones may carry RF repeaters which, when combined with other such drones, may advantageously provide a platform for an outdoor ad-hoc wireless network. Some drone applications may include a computer processing/control module and a GPS tracking module. The computer processing/control module and the GPS tracking module may provide computer control and GPS guidance for transport of various payloads, for example, shipment of packages to specific addresses.

SUMMARY

Apparatus and associated methods relate to height-differentiated gas detection sensors attached to one or more tethers suspended from an unmanned air vehicle (UAV) platform. In an illustrative example, each of the gas sensors, for example, may communicate gas detection signal information to a signal processing module onboard the UAV platform. Each of the tethers, for example, may provide a data channel from the sensor to the signal processing module. Some tethers, for example, may supply operating power to one or more of the gas detection sensors. The UAV platform may advantageously deploy one or more low-cost, disposable, tethered gas detection sensors into vertically confined spaces (e.g., chimneys, vents), or along a length of pipeline, for example. The sensors may be deployed at a minimum predetermined height providing separation from the UAV to attenuate prop-wash with respect to the sensors.

Various embodiments may achieve one or more advantages. For example, a UAV platform with suspended gas sensors may provide a disposable solution in harsh or abusive environments where the sensor may be damaged or lost. In such embodiments, the high-dollar-value drone may hover a safe distance from the harsh environment, while measurements may be taken from a tethered sensor within the harsh environment. Further, a predetermined minimum tether length may provide separation between the UAV and a gas measurement zone such that prop-wash from the UAV propellers may be mitigated with respect to the gas measurement.

In some embodiments, height-differentiated gas sensors suspended from a UAV may simultaneously detect gases of various specific gravities. Simultaneous detection may mitigate temporal delays between the detected gas intensities at varying heights increasing the validity of the information provided. Simultaneous detection may also minimize flight time, and may increase sensor positioning accuracy. Further, users may choose a sensor type to suit the application, for example, the sensors may be optimized to detect gas species which are expected to appear at differentiated heights.

In some implementations, more advantages may be achieved, for example, the UAV platform may collect raw data in real-time and send the data to a main platform where more processing power may be available. In some examples, the main platform may include higher data storage capacity, or may include higher RF transmission power capacity. The main platform may receive the raw data, perform data processing, and may transmit the processed data to a remote station. Some embodiments may be advantageously deployed to provide gas sensing in areas that are dangerous or inaccessible to humans. In situations requiring a large detection area, the UAV platform with suspended gas sensors may provide a low-cost alternative to covering the area with gas sensor installations.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, the tethered, gas detection sensors in typical use cases are briefly introduced with reference to FIGS. 1-3. Second, with reference to FIGS. 4-7, the discussion turns to exemplary functional block diagrams.

Figure 1:
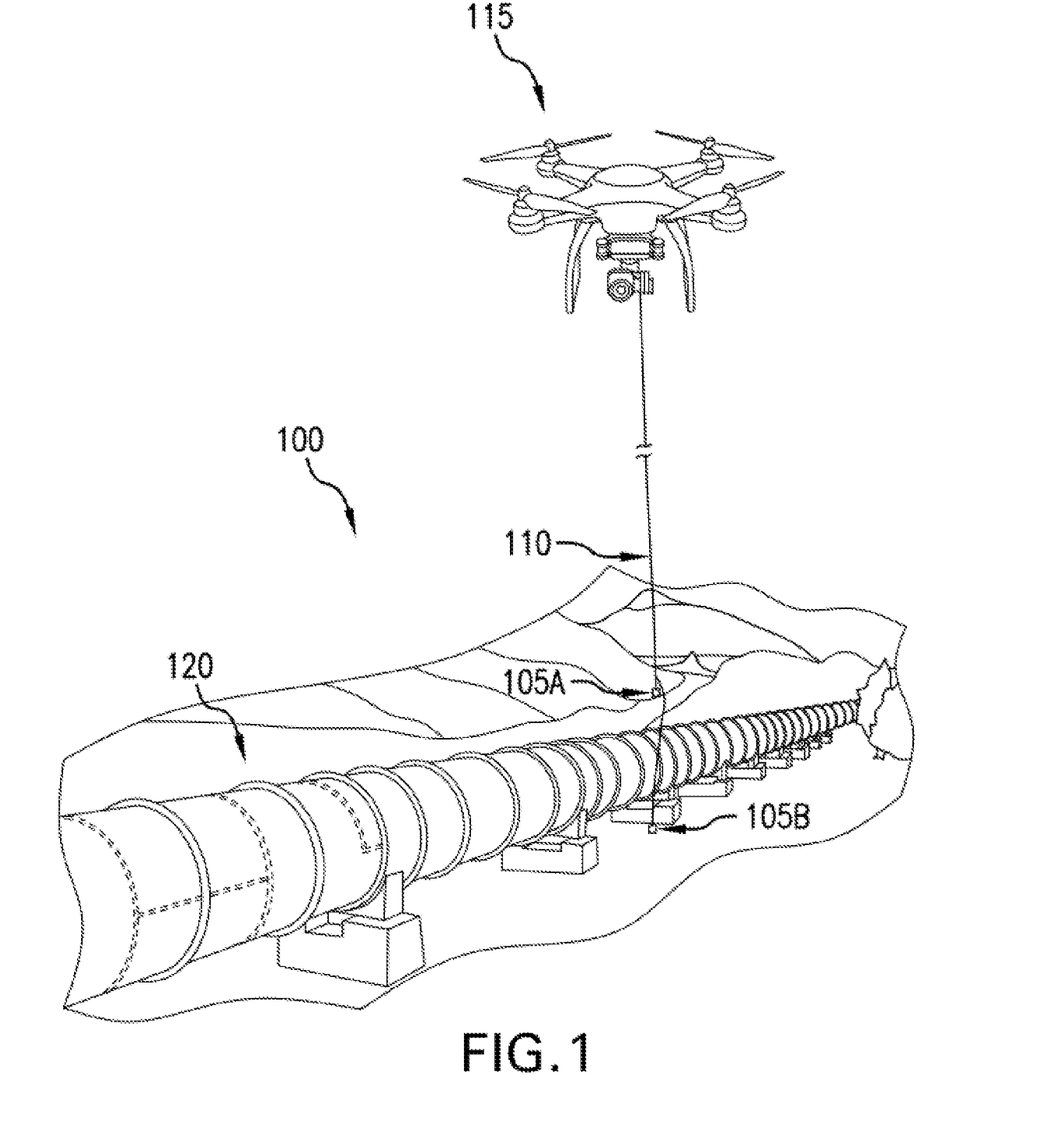
FIG. 1 depicts a perspective view of exemplary height-differentiated gas sensors tethered to an unmanned aerial vehicle (UAV) monitoring air-quality above and below a long length of pipeline.

FIG. 1 depicts a perspective view of exemplary height-differentiated gas sensors tethered to an unmanned aerial vehicle (UAV) monitoring air-quality above and below a long length of pipeline. A routine air-quality inspection 100 includes a pair of tethered gas detection sensors 105A and 105B. The tethered gas detection sensors 105A and 105B are fixedly coupled to a tether 110. The tether 110 is operably coupled to and supported by a UAV 115. In operation, the UAV 115 is remotely operated, flying along a length of a pipeline 120. The UAV 115 carrying the gas detection sensors 105A and 105B on the tether 110 may be deployed to detect the air-quality proximate to the pipeline 120.

Employment of the UAV 115 to carry the gas detection sensors 105A and 105B may advantageously enable a user to monitor gases over wide environments, such as the length of pipeline 120 shown in the depicted example. In an illustrative example, the UAV 115 may carry the gas detection sensors 105A and 105B over large areas, scanning the area by flying over it. In some examples, the UAV 115 may be deployed in lieu of personnel in cases of dangerous environments, and/or inaccessibility (e.g., flooded areas, mountains, deep ravines, crevices, caverns, off-shore oil platforms).

Employment of multiple gas detection sensors 105A and 105B may advantageously target detection of gases with various specific gravities. For example, to detect sulfur dioxide, the gas detection sensor 105B may be located near the ground, however to detect carbon monoxide, the gas detection sensor 105A may be located further away from the ground than the gas detection sensor 105B. In some embodiments, two or more gas detection sensors 105A and 105B may be deployed from the UAV 115 and may advantageously provide detection of gases near the ground and far above the ground.

The tether 110 may suspend the gas detection sensors 105A and 105B at a predetermined height below the UAV 115, which may advantageously attenuate the effects of prop-wash from the propeller on the UAV 115. The prop-wash rejection ratio may be at least about 20 dB, 25 dB, 30 dB, 35 dB, 40 dB, 45 dB, 50 dB, 55 dB, 60 dB, 65 dB, 70 dB, 75 dB, 80 dB, 90 dB or up to at least about 100 dB, for example. The prop-wash rejection ratio may be calculated by the formula $20*\log(GT/GD)$, where GT is the true gas concentration and GD is the amount of gas concentration deviation. In an illustrative example, a deviation of 0.1% equates to a prop-wash rejection of 60 dB.

Figure 2:
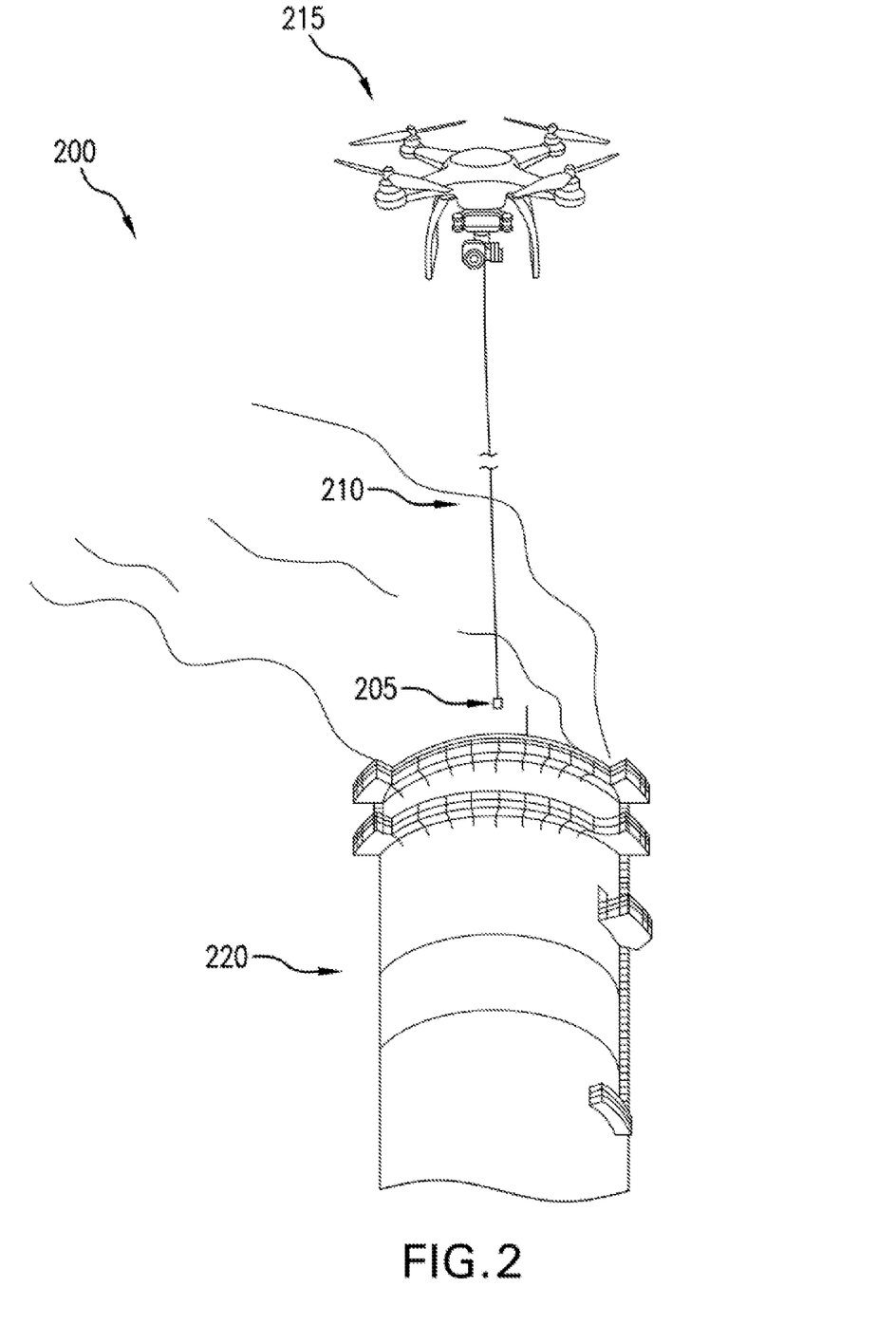
FIG. 2 depicts a perspective view of an exemplary gas sensor tethered to a UAV monitoring air-quality within a vertically confined industrial chimney stack.

FIG. 2 depicts a perspective view of an exemplary gas sensor tethered to a UAV monitoring air-quality within a vertically confined industrial chimney stack. A chimney stack emission inspection scenario 200 involves a low-cost, disposable gas detection element 205. The gas detection element 205 is operably coupled to and suspended by a tether 210. The tether 210 is operably coupled to and supported by a UAV 215. The UAV 215 hovers over a chimney stack 220, floating the gas detection element 205 directly over the opening of the chimney stack 220. As the UAV 215 maintains a safe distance from the emissions from the chimney stack 220, it lowers the gas detection element 205 into the narrow vertical confines of the chimney stack 220. Because the gas detection element 205 is low-cost and disposable, the user may advantageously lower the gas detection element 205 into potentially damaging environments without a substantial financial impact associated with replacing or repairing the relatively expensive drone platform. In addition, the UAV 215 deployment of the gas detection element 205 allows timely gas measurement without human labor and without putting personnel in harm's way.

Figure 3:
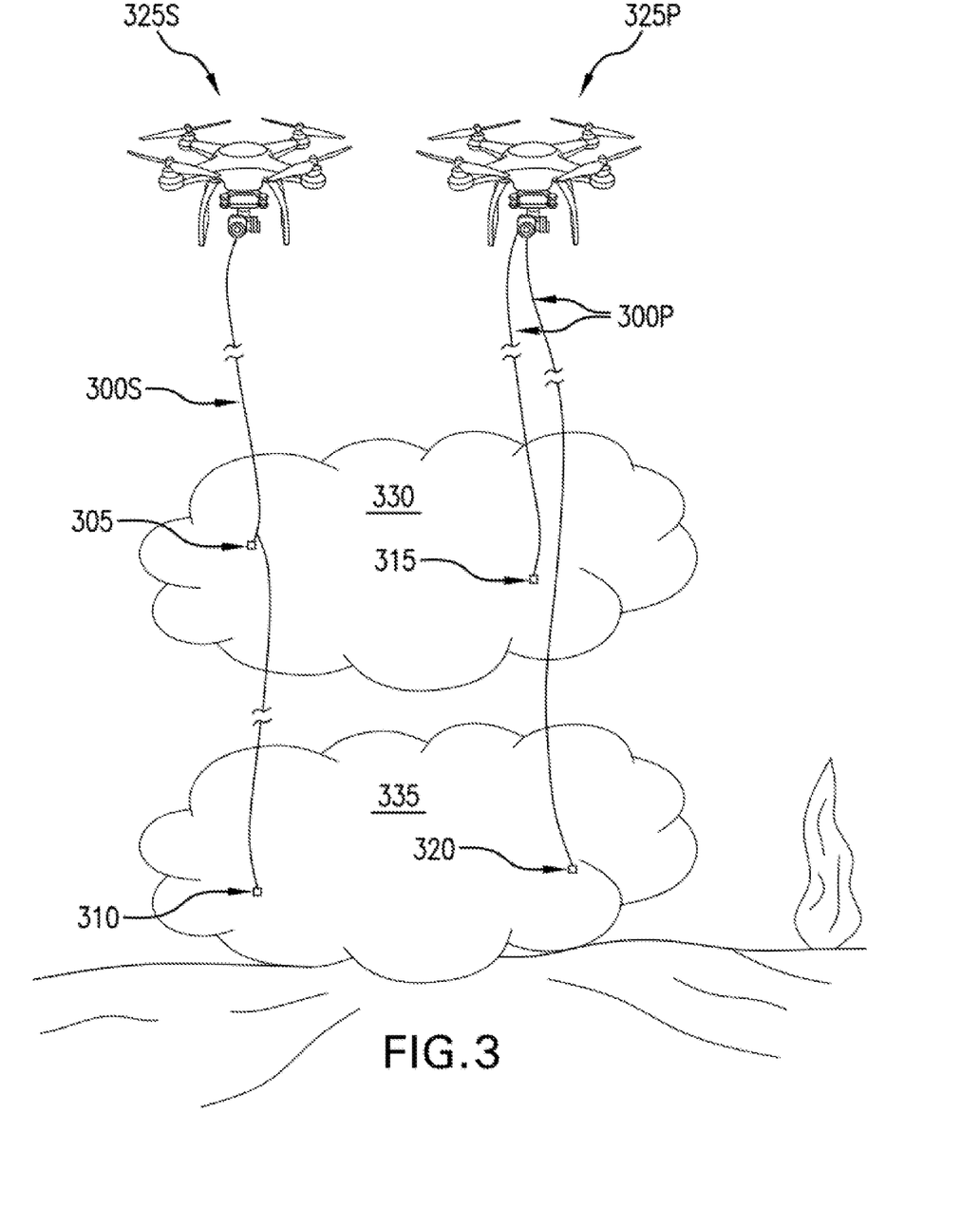
FIG. 3 depicts a perspective view of an exemplary series-connected deployment and exemplary parallel deployment of height-differentiated gas sensors tethered to a UAV.

FIG. 3 depicts a perspective view of an exemplary series-connected deployment and an exemplary parallel deployment of height-differentiated gas sensors tethered to a UAV. A series connected tether 300S includes an upper sensor 305 and a lower sensor 310. Users may find advantage in the series connected tether 300S, for example, the lower sensor 310 may track the upper sensor 305. Such tracking may advantageously allow sensing of gases directly above and below each other.

A parallel connected tether 300P includes an upper sensor 315 and a lower sensor 320. Users may find advantage in the separate tethering of the parallel connected tether 300P, for example, if one of the sensors 315 or 320 is somehow separated from the tether 300P, the other sensor 315 or 320 may continue to operate.

Each of the tethers 300S and 300P are suspended by a respective UAV 325S and 325P. Each of the tethers 300S and 300P are suspended over a gas 330 with a relatively low specific gravity and a gas 335 with a relatively high specific gravity. The upper sensors 305 and 315 may advantageously be optimized to detect the lighter gas 330. The lower sensors 310 and 320 may be optimized to detect the heavier gas 335.

Figure 4:
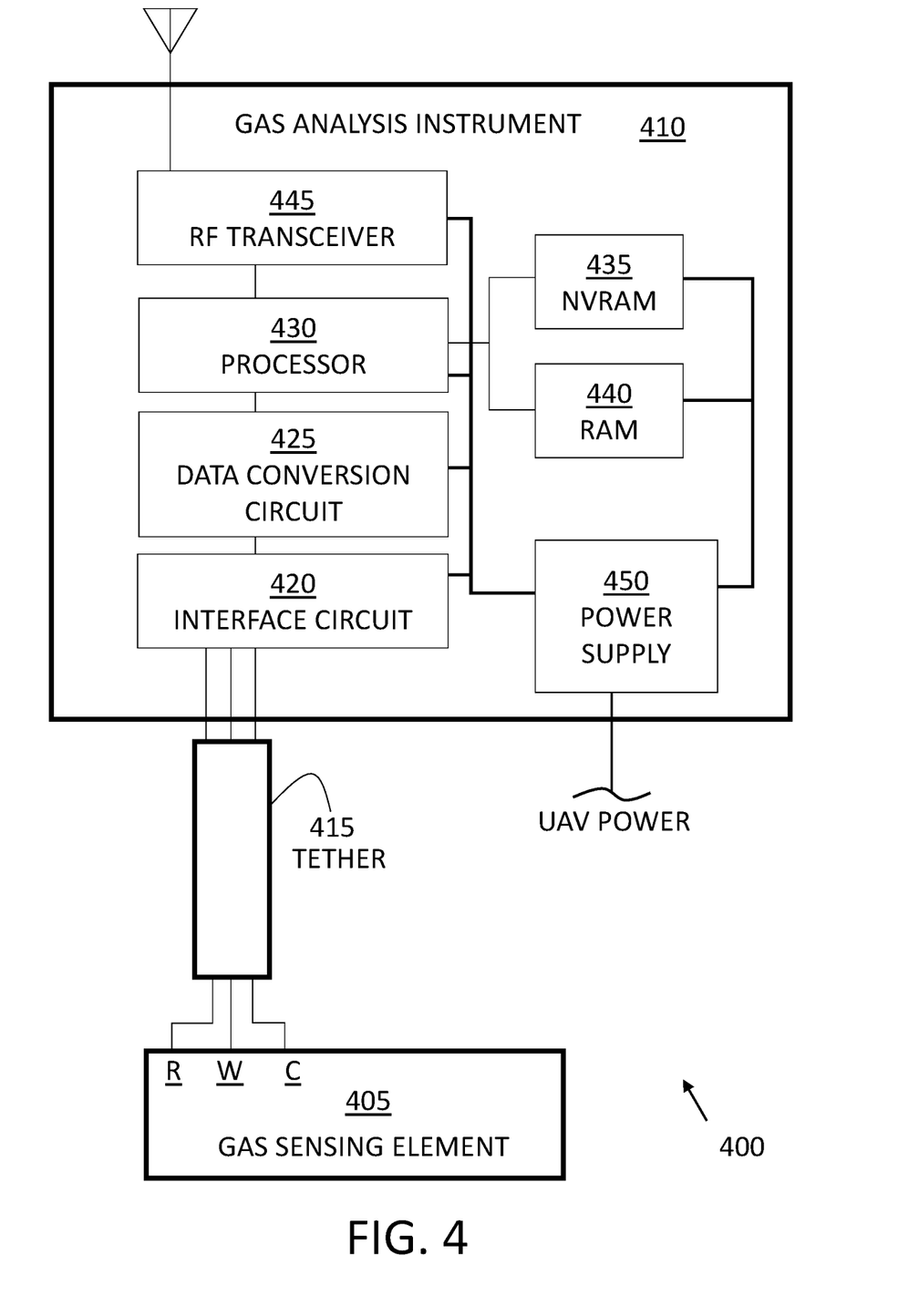
FIG. 4 depicts a block diagram view of a passive electrical gas sensing element tethered to a gas analysis instrument onboard a UAV.

FIG. 4 depicts a block diagram view of a passive electrical gas sensing element tethered to a gas analysis instrument onboard a UAV. A gas data collection and transmission system 400 includes a gas sensing element 405. The gas sensing element 405 may be a gas sensing module. The gas sensing element 405 may be a low-cost, disposable element. In the depicted example, the gas sensing element 405 may include an electrolyte engaged with a reference electrode R, a working electrode W and a counter electrode C. The electrodes R, W and C are operably coupled to a gas data collection and transmission instrument 410 via a tether 415.

In various embodiments, a gas data collection and transmission instrument (e.g., 410) on board a UAV may provide the electronics necessary to capture a signal from a gas sensing element (e.g., 405) on a tether (e.g., 300S, 300P) and to send the signal in a wireless transmission. The on-board electronics may be optimized to eliminate weight. Off-board, a ground-based transceiver may receive the wireless transmission, demodulate the transmission and send a resulting signal to a processing engine. The ground-based transceiver may include the processing engine. Accordingly, the overall payload of the UAV may be reduced by placing the heavier processing engine off-board the UAV. Various embodiments may collect and/or transmit data on the UAV in the most weight-effective manner. Data from a converted signal may be sent real-time or may be sent in batches. In some implementations, the collection and transmission functions may be placed on the UAV, as far away from the low-cost sensing element as practical.

In some examples, wires connected to the electrodes R, W and C are the tether 415. In various examples, wires connected to the electrodes R, W and C are housed within or around the tether 415. The gas data collection and transmission instrument 410 may be onboard a UAV. The gas sensing element 405 may be substantially light-weight, which may advantageously reduce the UAV payload, and accordingly, may reduce the propulsion power from the supporting UAV.

The signals from the electrodes R, W and C are sent to the gas data collection and transmission instrument 410 though an interface circuit 420. The interface circuit 420 conditions the signals from the gas sensing element 405 and produces an analog output which is fed to a data conversion circuit 425. The data conversion circuit 425 is operable to convert the analog signal from the interface circuit 420 into a digital value. The digital value from the data conversion circuit 425 is read by a processor 430. The processor 430 executes preprogrammed instructions from a nonvolatile random-access memory (NVRAM) 435. The processor 430 is operably connected to a random-access memory (RAM) 440. The RAM 440 provides basic memory access for the processor 430.

The processor 430 is operably connected to an RF transceiver 445. The RF transceiver 445 receives processed gas sensing data from the processor 430. The RF transceiver 445 transmits the data to a receiving device (not shown). In an illustrative example, the receiving device may store or further process the received data from the RF transceiver 445. In some embodiments, the processed gas sensing data from the processor 430 is saved in the RAM 440 and/or in the NVRAM 435. In such embodiments, the data may be retrieved from the gas data collection and transmission instrument 410 when the UAV returns from its mission. The interface circuit 420, the data conversion circuit 425, the processor 430, the NVRAM 435, the RAM 440, and the RF transceiver 445, all receive power from a power supply 450. The power supply 450 is sourced by a UAV power system. In some examples, the power supply 450 may be sourced by one or more UAV power systems.

In some examples, the processing engine may be located on-board the UAV. A light-weight processor (e.g., 430) used to collect the data/signals from the sensor on the tether, and used to send the data/signals to an RF transceiver (e.g., 445) may also be a processing engine used to process and analyze the signals.

Figure 5:
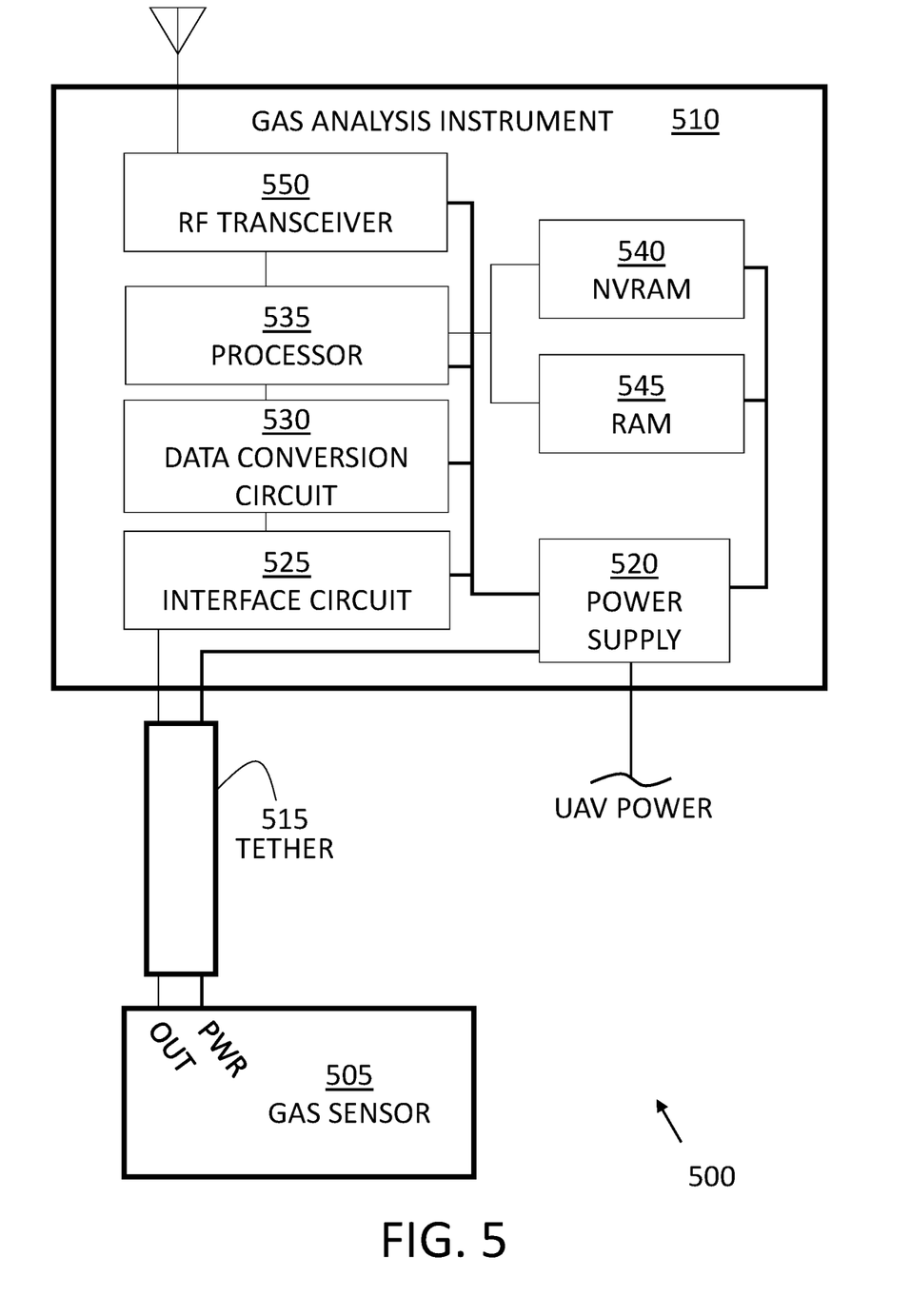
FIG. 5 depicts a block diagram view of an active electrical gas sensor tethered to a gas analysis instrument onboard a UAV.

FIG. 5 depicts a block diagram view of an active electrical gas sensor tethered to a gas analysis instrument onboard a UAV. A gas analysis system 500 includes a gas sensor 505. The gas sensor element 505 may be a gas sensing module. The gas sensor 505 is operably coupled to a gas analysis instrument 510 via a tether 515. The gas analysis instrument 510 may be a processing platform. The gas analysis instrument 510 is operable to power the gas sensor 505 with a power supply 520, and to receive a gas signal from the gas sensor 505.

The gas signal is received by the gas analysis instrument 510 through an interface circuit 525. The interface circuit 525 may operably protect the gas analysis instrument 510 from various electromagnetic interference (EMI) and may further condition the signal from the gas sensor 505. In response to the signal from the gas sensor 505, the interface circuit 525 produces an analog output which is fed to a data conversion circuit 530. The data conversion circuit 530 is operable to convert the analog signal from the interface circuit 525 into a digital value. The digital value from the data conversion circuit 530 is read by a processor 535.

The processor 535 executes preprogrammed instructions from a nonvolatile random-access memory (NVRAM) 540. The processor 535 is operably connected to a random-access memory (RAM) 545. The processor 535 is operably connected to an RF transceiver 550. The gas sensor 505, the interface circuit 525, the data conversion circuit 530, the processor 535, the NVRAM 540, the RAM 545, and the RF transceiver 550, all receive power from the power supply 520. The power supply 520 is sourced by a UAV power system.

The gas sensor 505 may include a gas sensing element (e.g., FIG. 4, item 405), and may include active circuitry powered by the power supply 520. Within the gas sensor 505, the active circuitry may be operable to receive the signals from the gas sensing element, which the active circuitry may filter, amplify, and/or transform. Further the active circuitry may drive a resulting signal up the tether 515 to the interface circuit 525. The active circuitry on the gas sensor 505 may advantageously provide a low-noise electrical signal (representing the ambient gas concentration) to the gas analysis instrument 510. The electrical signal may be produced with substantially wide dynamic range. The wide dynamic range may aid the circuits in the gas data collection and transmission instrument 410 in making substantially high-resolution gas measurements.

Figure 6:
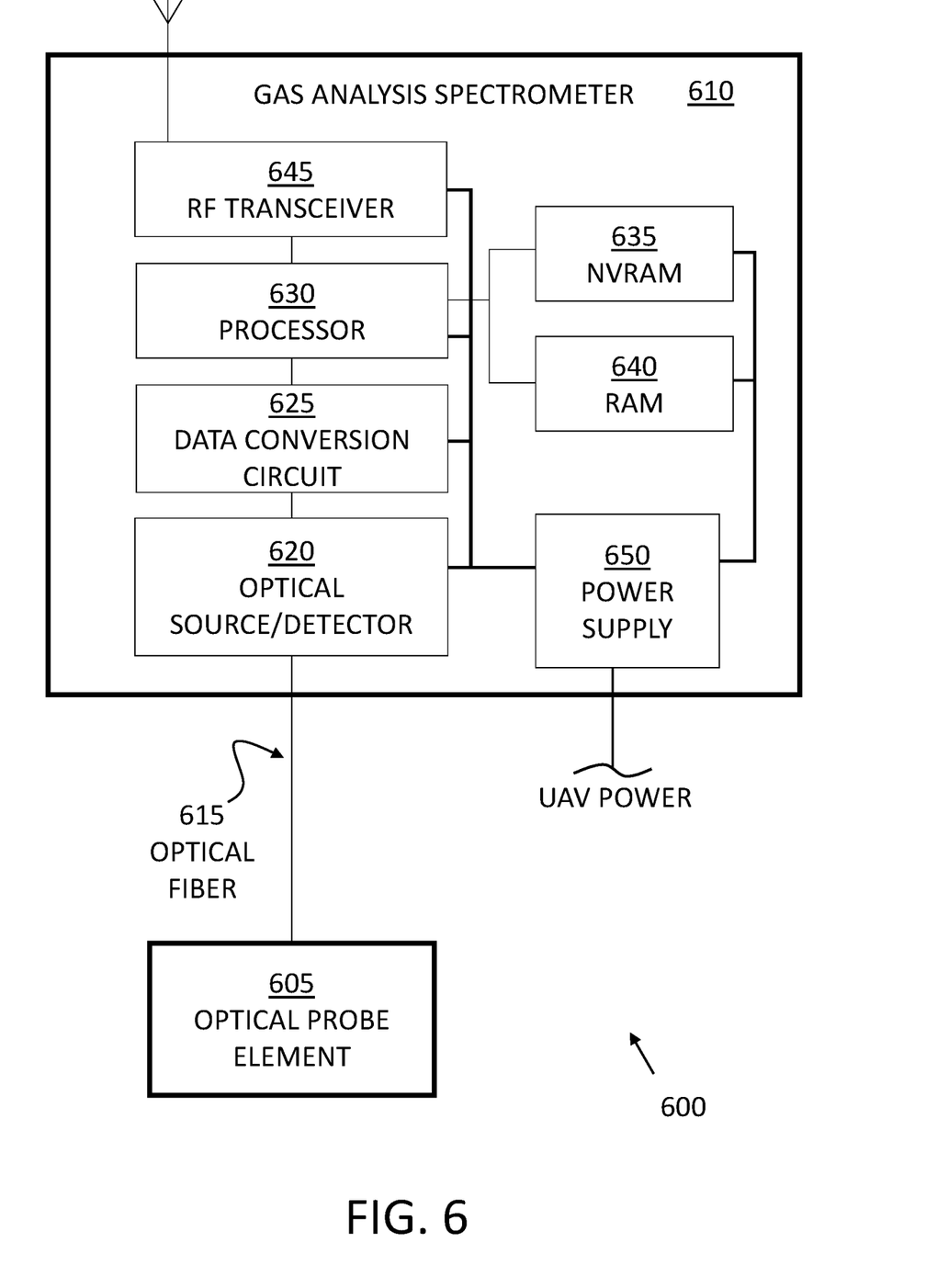
FIG. 6 depicts a block diagram view of an optical gas sensing element tethered to a gas analysis instrument onboard a UAV.

FIG. 6 depicts a block diagram view of an optical gas sensing element tethered to a gas analysis instrument onboard a UAV. An optical gas analysis system 600 includes an optical probe element 605. The optical probe element 605 may be a gas sensing module. The optical probe element 605 may be a low-cost disposable element. The optical probe element 605 is optically coupled to a gas analysis spectrometer 610 via an optical fiber 615. The gas analysis spectrometer 610 may be a processing platform. In some examples, the optical fiber 615 may be a tether. In some examples the optical fiber 615 may reside within or around a tether. The gas analysis spectrometer 610 may be onboard a UAV. In some implementations, the optical probe element 605 may be an optical microelectromechanical system (MEMS). Such MEMS devices may function like a miniature optical spectrometer-on-a-chip.

The optical probe element 605 is coupled to the distal end of the optical fiber 615. In some examples, the end of the optical fiber 615 may be the optical probe element 605. The optical fiber 615 may be adapted to carry light energy from an optical source/detector 620 to the optical probe element 605, where the light may reflect off various gases in the ambient environment. The reflected light may then be channeled back into the fiber where it may travel back to the optical source/detector 620. The optical probe element 605 may be substantially light-weight, which may advantageously reduce the UAV payload, and accordingly, may enable low propulsion power from the supporting UAV.

In various examples, the optical fiber 615 may be adapted to carry light energy from the optical source/detector 620 to the optical probe element 605, where various wavelengths of the light may be absorbed by various gases in the ambient environment. The remaining light wavelengths may then be channeled back into the fiber where it may travel back to the optical source/detector 620. Further, various optical detection methods may be employed (e.g., refraction, polarization). In some implementations, various changes in the properties of the light may be employed for gas detection, data collection and/or determination.

The optical source/detector 620 transforms, amplifies and filters the reflected light signals from the optical probe element 605 producing an analog output which is fed to a data conversion circuit 625. The data conversion circuit 625 is operable to convert the analog signal from the optical source/detector 620 into a digital value. The digital value from the data conversion circuit 625 is read by a processor 630. The processor 630 executes preprogrammed instructions from a nonvolatile random-access memory (NVRAM) 635. The processor 630 is operably connected to a random-access memory (RAM) 640. The RAM 640 provides basic memory access for the processor 630. The processor 630 is operably connected to an RF transceiver 645. The RF transceiver 645 receives processed gas sensing data from the processor 630. The RF transceiver 645 transmits the data to a receiving device (not shown).

In some examples, the end of the optical fiber 615 may itself be the optical probe element 605. The optical gas analysis system 600 may employ various techniques with this bare distal-end fiber 615. For example, optical fiber temperature sensing methods may be used with coated fiber methods. The methods may be a technique to produce gas concentration signals/data. This technique may be low-cost and disposable. Further this technique may be employed in height-differentiated gas sensing and in vertically confined spaces.

In an illustrative example, the receiving device may be operably coupled with a second processing device which may store or further process the received data from the RF transceiver 645. In such examples, the optical signals from the optical probe element 605 may be detected with the gas analysis spectrometer 610 on-board the UAV, and the actual analysis determining the gas type and/or gas concentrations may be executed in the second processing device.

In some embodiments, the processed gas sensing data from the processor 630 may be saved in the RAM 640 and/or in the NVRAM 635. In such embodiments, the data may be retrieved from the RAM 640 and/or the NVRAM 635 included in the gas analysis spectrometer 610 when the UAV returns from its mission. The optical source/detector 620, the data conversion circuit 625, the processor 630, the NVRAM 635, the RAM 640, and the RF transceiver 645, all receive power from a power supply 650. The power supply 650 is sourced by a power system onboard a UAV. In various examples, the power supply 650 may be sourced by one or more power systems onboard the UAV.

The detection system may implement an analysis based on colorimetric principles. The colorimetric principles can be applied to determine the concentration of various gases in an ambient environment. For example, a reagent may be added to a gas sample to produce a specific color. In such examples, the color intensity may be a function of the gas concentration. Accordingly, the color intensity may be measured photometrically to determine the gas concentration.

Figure 7:
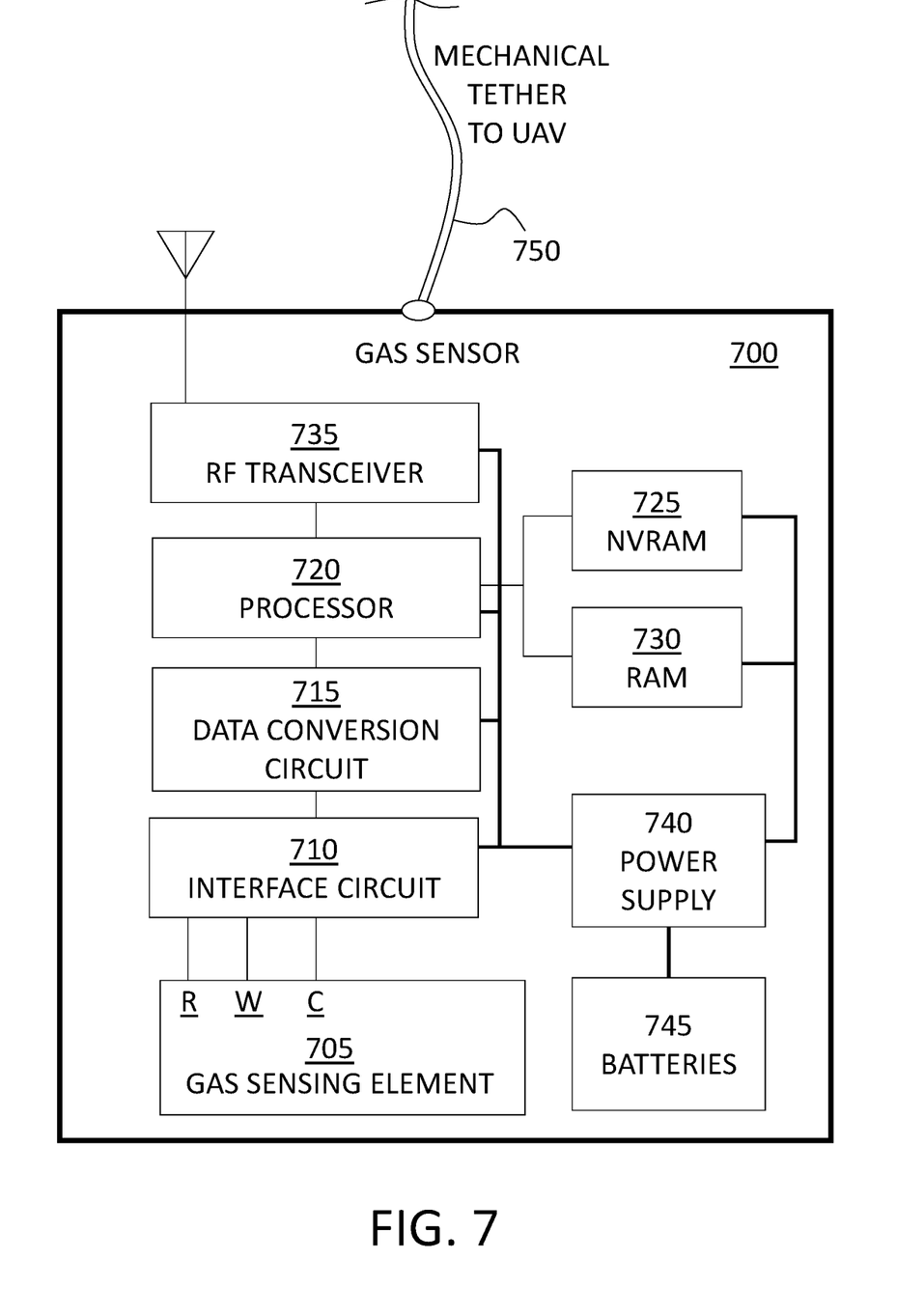
FIG. 7 depicts a block diagram view of a wireless gas sensor.

FIG. 7 depicts a block diagram view of a wireless gas sensor. A gas sensor 700 includes a gas sensing element 705. The gas sensor 700 may be a gas sensing module. The gas sensing element 705 includes an electrolyte engaged with a reference electrode R, a working electrode W and a counter electrode C. The electrodes R, W and C are operably coupled to an interface circuit 710. The gas sensor 700 may be substantially light-weight, which may advantageously reduce a UAV payload, and accordingly may enable low propulsion power from the supporting UAV.

The signals from the electrodes R, W and C are sent to the interface circuit 710. The interface circuit 710 conditions the signals from the gas sensing element 705, producing an analog output which is fed to a data conversion circuit 715. The data conversion circuit 715 is operable to convert the analog signal from the interface circuit 710 into a digital value. The digital value from the data conversion circuit 715 is read by a processor 720. The processor 720 executes preprogrammed instructions from a nonvolatile random-access memory (NVRAM) 725. The processor 720 is operably connected to a random-access memory (RAM) 730. The RAM 730 provides basic memory support for the processor 720.

The processor 720 is operably connected to an RF transceiver 735. The RF transceiver 735 receives processed gas sensing data from the processor 720. The RF transceiver 735 transmits the data to a receiving device (not shown). In an illustrative example, the receiving device may store or further process the received data from the RF transceiver 735. The receiving device may be located on-board the UAV, which may advantageously reduce the power consumption of the RF transceiver 735, and may therefore reduce the overall weight of the gas sensor 700. The receiving device may be located off-board the UAV, for example, located on a land-based transceiver. The off-board receiving device may advantageously reduce the payload of the UAV by absence of an on-board transceiver.

In some embodiments, the processed gas sensing data from the processor 720 may be stored in the RAM 730 and/or in the NVRAM 725. In such embodiments, the data may be retrieved from the gas sensor 700 when the UAV returns from its mission. The interface circuit 710, the data conversion circuit 715, the processor 720, the NVRAM 725, the RAM 730, and the RF transceiver 735, all receive power from a power supply 740. The power supply 740 is sourced by one or more batteries 745.

The batteries 745 may include various chemistries, for example, nickel-metal hydride (NiMH), which may advantageously provide high charge capacity. In some embodiments, the battery chemistry may be nickel-cadmium (Ni-Cad) which may advantageously provide a high number of charge cycles. Some examples may employ lithium-polymer (LiPo) which may provide light weight. Still other examples may employ lithium-ion (Li-Ion) which may advantageously be available in popular form factors. In some implementations, lithium iron phosphate (LiFePO4) batteries may be used, which may advantageously provide a very high number of charge cycles, and provide higher output voltage. In various examples, the gas sensor 700 may incorporate power sources other than internal batteries. These examples may include solar power sources, kinetic energy harvesting, rechargeable batteries or capacitors.

The batteries 745 may include common batteries sizes (e.g., A, AA, 9V, coin) which the user may personally obtain. These sizes may use various battery chemistries such as alkaline, carbon, carbon-zinc, zinc-chloride and lithium. The batteries 745 may be re-chargeable. As such, the power source may include a charging cord that plugs into a power source, (e.g., USB port).

The gas sensor 700 is mechanically supported by a UAV via a tether 750. In the depicted example, the tether 750 may provide mechanical support only. The gas sensor 700 which is mechanically tethered to a UAV, includes the sensing components, the data collection components, the processing components, and the wireless components, which may advantageously enable it to autonomously process and send wireless signals indicative of gases and/or gas concentrations sensed in its ambient environment.

In some examples, the wireless signals may produce a data link between the gas sensor 700 and a transceiver on-board the UAV. The wireless data link between the gas sensor 700 and the UAV transceiver may advantageously avoid electromagnetic interference due to the absence of an active tether, which may have acted as an antenna, picking up electromagnetic interference. The wireless data link between the gas sensor 700 and the UAV transceiver may advantageously avoid breakage of an otherwise active wired tether. The wireless data link between the gas sensor 700 and the UAV may advantageously allow implementation of flexible tethers which may be advantageously spooled onto the UAV. The UAV may control the motion of the spool(s) which may advantageously allow the UAV to control the deployment height of the gas sensor 700. In examples of two or more spools on-board the UAV, the height-differentiation between deployed gas sensors may also be controlled.

Accordingly, in some examples, a UAV gas sensing system may employ a low-cost optical communication link used to communicate up and down a fiber communication tether. In some examples, the gas sensor 700 may include a low-cost infrared (IR) light emitting diode (LED) transmitting system. The optical communication link may mitigate radio frequency interference (RFI). The mitigation of RFI may provide a substantially clean sensor signal to the receiving device on-board the UAV. The fiber communication tether discussed in this example may be distinct from the optical fiber 615 in FIG. 6, where the optical fiber 615 is integral to the sensing technique.

In various examples, a UAV gas sensing system may locate various gas sensing components on the UAV end (e.g., proximal end) of a tether. Location of components on the UAV end may advantageously position the center of gravity of the overall system closer to the UAV. Further, a heavy payload located at the UAV may provide UAV operators straight-forward and stable positional control.

In some implementations, the wireless signals may produce a data link between the gas sensor 700 and a ground-based transceiver coupled to a computer. Communication direct to a ground-based transceiver may advantageously reduce weight on the UAV, avoiding an on-board UAV transceiver. Communication direct to a ground-based transceiver may advantageously reduce the cost of the UAV and thereby the cost of damage, in the event of a UAV crash or loss, for example.

Figure 8:
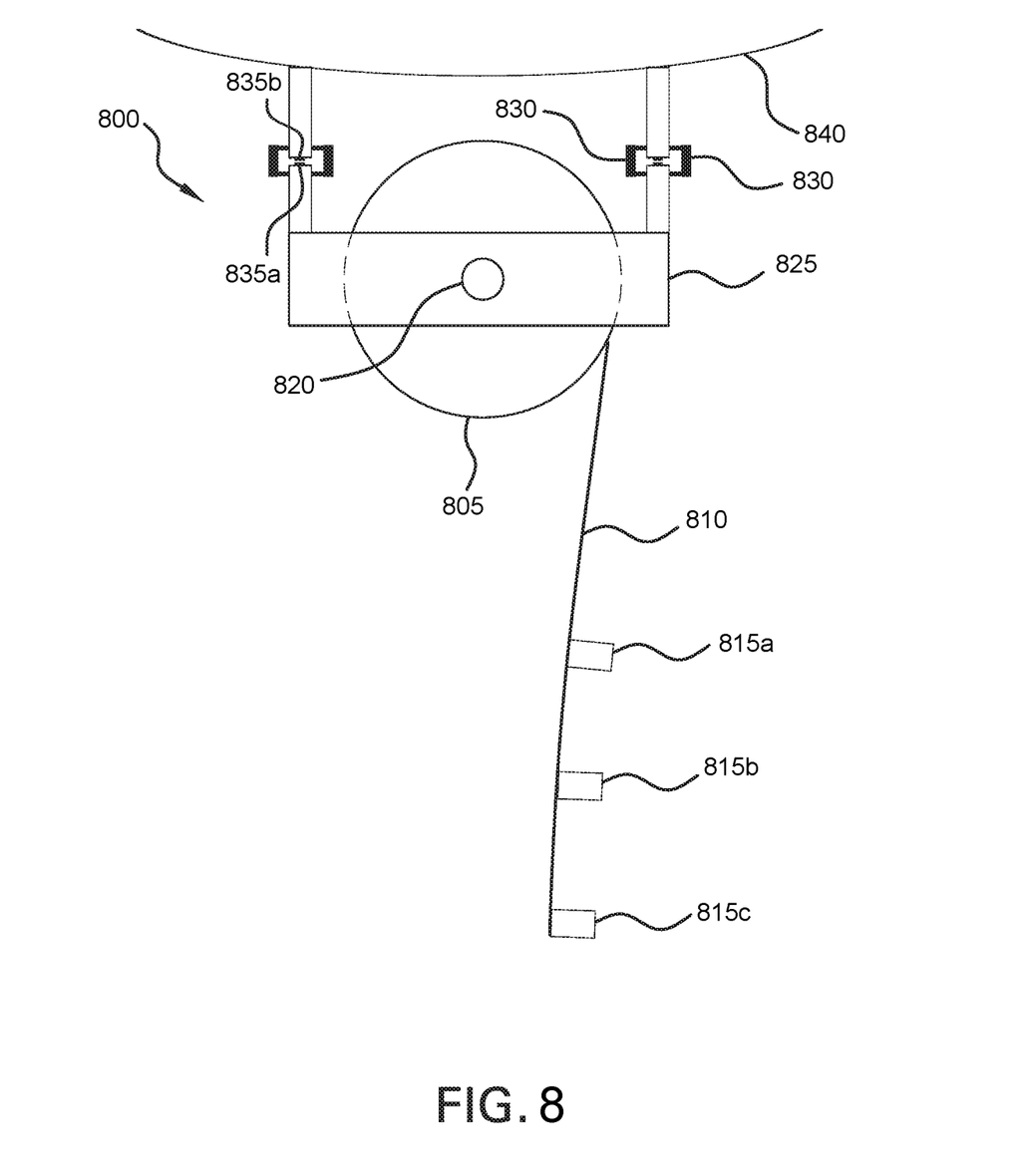
FIG. 8 depicts a side view of an exemplary retraction and release system for a tether coupled to a UAV.

FIG. 8 depicts a side view of an exemplary retraction and release system for a tether coupled to a UAV. A retraction and release system 800 includes a spool 805. Wound around the spool 805 is a tether 810. Coupled to the tether 810 are a plurality of gas detection sensors 815*a*, 815*b*, and 815*c*. The spool 805 is configured to rotate via a spool shaft 820. The spool shaft 820 is coupled to a retraction support structure 825. In operation, the winding of the spool 805 may be controlled by the UAV. For example, a user with a remote controller may send a command signal to the UAV which controls the spooling or unspooling of the tether 810. The UAV may allow for retraction or extraction of the tether 810, which may allow for on-the-fly customization of the height of each sensor 815*a*-815*c*. Configuring the height of each sensor 815*a*-815*c* may be advantageous in cases where more or less tether length is needed to accomplish a specific job, task, or objective. For example, if a UAV is in route to a target destination, the tether 810 may be fully retracted to prevent unwanted drag or minimize the chance of the tether being caught on a structure (such as a power line, for example). When the UAV reaches the target destination (e.g., a smoke stack to inspect), the tether 810 may be unwound from the spool 805 to perform gas detection (e.g., within the interior of the smoke stack). Once inspection is complete, the tether 810 may be rewound with the spool 805 for travel back to a home point.

The retraction and release system 800 includes at least one locking/releasing mechanism 830 configured to releasably lock the tether 810 with a UAV 840. In some example, the locking mechanism 830 may be a clamp that can open/close to release/lock the tether from/with the UAV 840. The mechanism 830 may be controlled by the UAV 840 (perhaps via a controller that controls the UAV), such that a user can selectively determine whether the tether is coupled with the UAV or whether the tether should be decoupled from the UAV. The mechanism 830 may advantageously allow the UAV or a controlling user to selectively decouple the tether 810 from the UAV 840 in a situation where it may be dangerous to maintain the coupling between the tether 810 and the UAV 840. For example, if the tether 810 becomes wrapped around a tree and cannot be separated from the tree, then a user may send a command to the UAV to decouple the tether 810 from the UAV. A decoupling order may save the UAV (which may be a relatively expensive item) from being damaged or lost, in exchange for abandoning the tether (which may be a relatively inexpensive item). In some examples, the mechanism 830 may be a releasable mechanical coupling that is configured to safely and purposefully break a connection between the tether 810 and the UAV 840 upon sufficient force/pressure without damage to the UAV. For example, if the tether 810 gets caught on a power line, then upon a predetermined force between the UAV and the tether, the tether may become uncoupled. In some examples, the tether may be configured to decouple from the UAV upon a force of at least 10 N, 20 N, 30 N, 40 N, or about 50 N or more.

The system 800 includes electrical interfaces 835*a*, 835*b*. A first electrical interface 835*a* (associated with the gas detection sensors) may be configured to transmit electrical signals from the sensors 815*a*-815*b* to the UAV 840 via the tether 810 and/or receive electrical signals from the UAV 840 to the sensors 815*a*-815*b* via the tether 810. A second electrical interface 835*b* (associated with the UAV) may be configured to transmit electrical signals from the UAV 840 to the sensors 815*a*-815*b* via the tether 810 and/or receive electrical signals from the sensors 815*a*-815*b* to the UAV 840 via the tether 810. The interfaces 835*a* and 835*b* may interface or physically connect with one another to facilitate electrical communication between the sensors 815*a*-815*c* and the UAV 840. For example, the interfaces 835*a* and 835*b* may be electrical pads or USB interfaces that touch or pluggably connect with one another. Data and/or power may be passed between the UAV 840 and the sensors 815*a*-815*c* via the tether. In some examples, the spool shaft 820 may integrate a slip-ring configured to pass electrical signals/power between the UAV and the tether 810.

Although various embodiments have been described with reference to the figures, other embodiments are possible. For example, the gas sensors tethered from a UAV may physically capture gas samples. In such embodiments, the UAV may be deployed by an operator to a site for gas sampling via remote control. Via remote control, the operator may command UAV to lower a gas sampling container. The container may be suspended and controlled via a tether. The container may be opened within a space to physically capture one or more gases that may be present. Via remote control, the operator may then close the gas sampling container. In some embodiments, the UAV may be preprogrammed to execute this physical gas sampling autonomously. The gas sampling container may then be retrieved by the UAV via the tether, and be transported back to the operator, for example.

Various optical gas sensing techniques may produce one or more advantages. For example, some techniques may combine a mechanical tether and a light transmission module where the light may pass to and/or from various analysis equipment. In such techniques, the light may be analyzed for various parameters (e.g., absorption, spectral wavelength intensity).

In some gas sensing techniques, a tether and/or a sensing element may be part of a distributed sensing system. For example, a MEMS gas sensing element may be suspended from a tether and may provide a signal (e.g., current, voltage, wireless transmission) in response to various gases to which the MEMS element is exposed. The signal may be sensed by interface circuits on-board a UAV producing a resulting signal. The resulting signal may be transmitted wirelessly by a transmitter on-board the UAV. The employed electronics may be light-weight which may advantageously reduce the overall payload of the UAV.

In an illustrative example, a UAV with sensors suspended from predetermined heights may be employed for industrial safety. In industries such as oil exploration, a UAV may be deployed quickly to areas that may be human-inaccessible or practically inaccessible. The UAV may be deployed to detect gas emissions from various gas carrying structures (e.g., pipes, valves, tanks, vents) on, in or under an oil drilling platform.

In the field of environmental pollution mapping, the UAV may economically scan large areas. In some instances, the areas may be flooded or marshy which may make human deployment of individual sensors difficult, expensive or dangerous. The UAV may include a global positioning system (GPS) and may log geographic location information along with the gas concentration level, creating a database characterizing a pollution map. In some embodiments the GPS may be included in a GPS tracking module.

In various implementations, the UAV with sensors suspended from predetermined heights may be employed in agricultural or forestry applications. Various gases within a farm crop may be present and may be detected using various methods. For example, farmers using anhydrous ammonia may monitor chemical drift. Further, in large forests, the UAV with sensors suspended from predetermined heights may detect various gases. For example, rangers may find benefit in detection of smoke in the initial stages of a forest fire. Also for example, rangers may detect concentrations of sulfur dioxide from nearby factories when monitoring for various pollutants harmful to forest plants and animals. In some examples, forest research personnel may study the effects of various gases on deforestation, or may be alerted to incipient natural or manmade disasters.

The UAV with suspended sensors may be useful in private or national security scenarios. For example, army troops may transport various gas detectors on a UAV to determine the safety of certain areas that are vertically confined, such as canyons, caves or tunnels. In some implementations, the perimeters of various outdoor venues may be scanned to detect various gases that may pose a risk to individuals or animals in public or private gatherings.

Due to the low-cost of sensor implementation, in some embodiments, the UAV may lower one or more "sacrificial" gas sensors into a known hazardous area. In such implementations, sensor deployment crews may experience very little cost impact if the sensor is destroyed, damaged and/or lost.

In various embodiments, a method of sampling ambient gas concentrations may be facilitated by deployment of a UAV. The UAV may include one or more gas sensing elements tethered to the UAV in such a manner to allow height-differentiated data (tethered at multiple heights). In an illustrative example, the tether may provide extrinsic conveyance of data, or may be an intrinsic part of the sensing, having an energy flow path in both directions. The gas sensing elements may process and transmit data autonomously, the tether providing mechanical support only. The gas sensor may include an RF transceiver, communicating from the sensor on the tether to a gas analysis instrument onboard the UAV.

Various embodiments may facilitate gas sensing over wide environments. Further, various examples of height-differentiated gas detection sensors suspended from a UAV platform may achieve broad "detection coverage" for a minimum number of detectors. The UAV transport may avoid the cost of implementing multiple sensors in multiple locations in such wide environments.

In some implementations, a UAV platform may collect raw data in real-time and send the data to a main platform where more processing power may be available. The main platform may receive the raw data, perform data processing, and may transmit the processed data to a remote station. The main platform and the remote station may be ground-based transceivers.

In an exemplary aspect, a field deployable sensor apparatus may include at least one gas sensing module, an unmanned aerial vehicle (UAV), a sensor receiving module coupled to a frame of the UAV, and at least one tether coupled on a proximal end to the sensor receiving module. The at least one tether may be further configured to support the at least one gas sensing module on a distal end. The at least one tether may be further configured to provide a sensor data path from the at least one gas sensing module to the sensor receiving module. The at least one gas sensing module may include one or more gas sensing modules placed at different heights along the tether. The at least one gas sensing module may be further configured to operate on optical signals. The one or more tethers may include optical fibers. The optical signals may be transmitted via the optical fibers of the at least one tether.

The at least one gas sensing module may be configured to produce an electrical current in response to exposure to a particular gas. The UAV may further include a GPS tracking module for tracking a location of the UAV. The system may further include a processing platform supported by the UAV frame, and may operatively couple to the at least one gas sensing modules. The at least one gas sensing module may be supplied with operating power from the UAV, via the at least one tether. The operating power supplied to the at least one gas sensing module may be solar power.

In an exemplary aspect, the system may include a UAV, one or more gas sensing modules, a sensor receiving module, and one or more tethers, which may be coupled to the frame of the UAV. The one or more tethers may be coupled at a proximal end to the sensor receiving module. The one or more tethers may each be coupled to a respective gas sensing module. Each of the one or more tethers may be configured to support a respective gas sensing module. The one or more tethers may be configured to provide one or more sensor data paths from a respective gas sensing module to the sensor receiving module.

Each of the tethers may be fixedly coupled to each of the gas sensing modules on a distal end. Each of the tethers may be fixedly coupled to the sensor receiving module at a proximal end. Each of the gas sensing modules may be configured to wirelessly communicate to a ground-based transceiver. In some embodiments, the sensor receiving module may communicate to the ground-based transceiver.

In some embodiments, the gas detection sensors attached to the tether may be placed at a height along the tether that substantially attenuates the prop wash disturbances created by the UAV. The phrase substantially attenuated in this context may mean that the velocity of air due to prop wash surrounding the sensor is about 50%, 25%, 10%, 5%, or about 1% of the velocity of air in the immediate vicinity of the propellers of the UAV.

A field-deployable sensor apparatus may include, in some exemplary aspects, an unmanned aerial vehicle (UAV), a tether suspended from the UAV, and at least one gas detection sensor coupled to the tether. The at least one gas detection sensor may include, for example, a plurality of gas detection sensors that may be disposed at different heights along the tether. The apparatus may include a sensor data receiving module fixedly coupled to the UAV and operably coupled with the at least one gas detection sensor to receive sensor data from the at least one gas detection sensor. In various examples, the sensor data receiving module may be operably coupled with the tether. The tether may include, for examples, at least one data communication pathway to facilitate the reception of sensor data by the sensor data receiving module. In various implementations, the at least one gas detection sensor may operate on optical signals and the at least one data communication pathway may include optical fiber, such that the optical fiber may be configured to transmit the optical signals to facilitate the reception of sensor data by the sensor data receiving module.

In some embodiments, the at least one gas detection sensor may be supplied with operating power from the UAV via the at least one tether. The tether, in various implementations, may be a purely mechanical tether without a data communication pathway. One of the at least one gas detection sensor may integrate a first wireless antenna. The UAV may, in an exemplary aspect, include a second wireless antenna operably coupled to the sensor data receiving module, such that the first antenna may be configured to wirelessly couple with the second antenna to facilitate the reception of sensor data by the sensor data receiving module.

In various examples, one of the at least one gas detection sensor may include a wireless antenna configured to transmit sensor data. In some implementations, the tether may be a first tether, the at least one gas detection sensor may be a first at least one gas detection sensor, and the field deployable sensor apparatus may further include a second tether and a second at least one gas detection sensor that may be coupled to the second tether. The tether may, for example, be releasably coupled to the UAV. In some implementations, the UAV is configured to selectively sever the coupling between the UAV and the tether.

In some examples, the at least one gas detection sensor may be coupled at a predetermined height along the tether to substantially attenuate the prop wash disturbance caused by a propeller of the UAV in the immediate vicinity of the at least one gas detection sensor. One of the at least one gas detection sensor may include a wireless antenna configured to transmit sensor data. The field deployable sensor apparatus may include a retraction means (e.g., a spool) for retracting the tether, the retraction means being coupled to the UAV. The apparatus may include a releasable locking mechanism for selectively locking the tether to, and selectively releasing the tether from, the UAV. The apparatus may include a releasable mechanical coupling between the tether and the UAV, the releasable mechanical coupling configured to safely and purposefully uncouple the tether from the UAV upon a predetermined amount of force, without damage to the UAV.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments may be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from a source to a first receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, FireWire, ATA/IDE, RS-232, RS-422, RS-485, 802.11 a/b/g/n, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various embodiments, a computer system may include non-transitory memory. The memory may be connected to the one or more processors may be configured for encoding data and computer readable instructions, including processor executable program instructions. The data and computer readable instructions may be accessible to the one or more processors. The processor executable program instructions, when executed by the one or more processors, may cause the one or more processors to perform various operations.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. A field-deployable sensor apparatus comprising:
   an unmanned aerial vehicle (UAV) having a signal processing module;
   a tether suspended from the UAV; and
   at least one gas detection sensor coupled to and suspended from the tether, wherein the at least one gas detection sensor comprises a plurality of gas detection sensors that are disposed at different heights along the tether,
   wherein the tether connects the at least one gas detection sensor and the signal processing module and provides a data channel between the at least one gas detection sensor and the signal processing module, wherein the signal processing module receives gas sensing data from the at least one gas detection sensor via the data channel and processes the gas sensing data,
   wherein the UAV further comprises a propeller, wherein a height from the at least one gas detection sensor to the UAV along the tether is determined based at least in part on a prop-wash rejection ratio associated with the propeller.

2. The field-deployable sensor apparatus of claim 1, further comprising a sensor data receiving module, wherein the sensor data receiving module is operably coupled with the tether and the tether comprises at least one data communication pathway to facilitate the reception of the gas sensing data by the sensor data receiving module.

3. The field-deployable sensor apparatus of claim 2, wherein the at least one gas detection sensor operates on optical signals and the at least one data communication pathway comprises optical fiber, such that the optical fiber is configured to transmit the optical signals to facilitate the reception of the gas sensing data by the sensor data receiving module.

4. The field-deployable sensor apparatus of claim 1, wherein the at least one gas detection sensor is supplied with operating power from the UAV via the tether.

5. The field-deployable sensor apparatus of claim 1, wherein:
   the tether comprises a purely mechanical tether without a data communication pathway,
   one of the at least one gas detection sensor comprises a first wireless antenna, and,
   the UAV comprises a second wireless antenna operably coupled to a sensor data receiving module, such that the first wireless antenna is configured to wirelessly couple with the second wireless antenna to facilitate the reception of the gas sensing data by the sensor data receiving module.

6. The field-deployable sensor apparatus of claim 1, wherein one of the at least one gas detection sensor comprises a wireless antenna configured to transmit the gas sensing data.

7. The field-deployable sensor apparatus of claim 1, wherein:
   the tether is a first tether,
   the at least one gas detection sensor is a first at least one gas detection sensor,
   the field-deployable sensor apparatus further comprises a second tether and a second at least one gas detection sensor that is coupled to the second tether.

8. The field-deployable sensor apparatus of claim 1, wherein the tether is releasably coupled to the UAV.

9. The field-deployable sensor apparatus of claim 8, wherein the UAV is configured to selectively sever coupling between the UAV and the tether.

10. The field-deployable sensor apparatus of claim 1, wherein the prop-wash rejection ratio is calculated based on 20 times log(GT/GD), wherein GT corresponds to a true gas concentration and GD corresponds to an amount of gas concentration deviation.

11. A field-deployable sensor apparatus comprising:
    an unmanned aerial vehicle (UAV) having a signal processing module;
    a tether suspended from the UAV; and
    at least one gas detection sensor coupled to and suspended from the tether,
    wherein the tether connects the at least one gas detection sensor and the signal processing module and provides a data channel between the at least one gas detection sensor and the signal processing module, wherein the signal processing module receives gas sensing data from the at least one gas detection sensor via the data channel and processes the gas sensing data, wherein the UAV further comprises a propeller, wherein a height from the at least one gas detection sensor to the UAV along the tether is determined based at least in part on a prop-wash rejection ratio associated with the propeller.

12. The field-deployable sensor apparatus of claim 11, further comprising a sensor data receiving module, wherein the sensor data receiving module is operably coupled with the tether and the tether comprises at least one data communication pathway to facilitate the reception of the gas sensing data by the sensor data receiving module.

13. The field-deployable sensor apparatus of claim 11, wherein the at least one gas detection sensor is coupled at a predetermined height along the tether to substantially attenuate a prop wash disturbance caused by the propeller of the UAV in an immediate vicinity of the at least one gas detection sensor.

14. The field-deployable sensor apparatus of claim 11, wherein one of the at least one gas detection sensor comprises a wireless antenna configured to transmit the gas sensing data.

15. The field-deployable sensor apparatus of claim 11, wherein:

the tether is a first tether, the at least one gas detection sensor is a first at least one gas detection sensor, the field-deployable sensor apparatus further comprises a second tether and a second at least one gas detection sensor that is coupled to the second tether.

16. The field-deployable sensor apparatus of claim 11, wherein the tether is releasably coupled to the UAV.

17. The field-deployable sensor apparatus of claim 11, further comprising a retraction means for retracting the tether, the retraction means being coupled to the UAV.

18. The field-deployable sensor apparatus of claim 11, further comprising a releasable locking mechanism for selectively locking the tether to, and selectively releasing the tether from, the UAV.

19. The field-deployable sensor apparatus of claim 11, further comprising a releasable mechanical coupling between the tether and the UAV, the releasable mechanical coupling configured to safely and purposefully uncouple the tether from the UAV upon a predetermined amount of force, without damage to the UAV.

20. The field-deployable sensor apparatus of claim 11, wherein the prop-wash rejection ratio is calculated based on 20 times log(GT/GD), wherein GT corresponds to a true gas concentration and GD corresponds to an amount of gas concentration deviation.

* * * * *